United States Patent
Wadhwa et al.

(10) Patent No.: US 10,039,526 B2
(45) Date of Patent: Aug. 7, 2018

(54) PIXEL RECEIVER WITH LOW FREQUENCY NOISE REDUCTION FOR ULTRASONIC IMAGING APPARATUS

(71) Applicant: QUALCOMM Incorporated, San Diego, CA (US)

(72) Inventors: Sameer Wadhwa, San Diego, CA (US); Lennart Karl-Axel Mathe, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 414 days.

(21) Appl. No.: 14/857,575

(22) Filed: Sep. 17, 2015

(65) Prior Publication Data
US 2017/0079624 A1   Mar. 23, 2017

(51) Int. Cl.
*A61B 8/00* (2006.01)
*A61B 8/08* (2006.01)
*A61B 8/14* (2006.01)
*G06K 9/00* (2006.01)

(52) U.S. Cl.
CPC ........... *A61B 8/5269* (2013.01); *A61B 8/14* (2013.01); *A61B 8/4494* (2013.01); *G06K 9/0002* (2013.01)

(58) Field of Classification Search
CPC ....... A61B 8/14; A61B 8/4494; A61B 8/5269; G06K 9/0002
See application file for complete search history.

(56) References Cited

U.S. PATENT DOCUMENTS

| | | | |
|---|---|---|---|
| 8,436,833 B2 | 5/2013 | King et al. | |
| 8,587,560 B2 | 11/2013 | Tateuchi et al. | |
| 2013/0063395 A1 | 3/2013 | Byun et al. | |
| 2014/0355387 A1 | 12/2014 | Kitchens, II et al. | |
| 2015/0123931 A1 | 5/2015 | Kitchens et al. | |
| 2017/0059699 A1* | 3/2017 | Mathe | A61B 5/117 |
| 2017/0079624 A1* | 3/2017 | Wadhwa | A61B 8/14 |

FOREIGN PATENT DOCUMENTS

WO   WO-2017048549 A1 *   3/2017  ............... A61B 8/14

OTHER PUBLICATIONS

Blake K., et al., "Amplifying High-Impedance Sensors-Photodiode Example", Microchip Technology Inc, Jan. 1, 2004 (Jan. 1, 2004), XP055320808, 14 pages. Retrieved from the Internet: URL: http://ww1.microchip.com/downloads/en/AppNotes/00951a.pdf.

(Continued)

*Primary Examiner* — Daniel Pihulic
(74) *Attorney, Agent, or Firm* — Loza & Loza, LLP (57) ABSTRACT

Apparatus and method for generating a DC pixel voltage are disclosed. The apparatus includes an amplifier configured to amplify an input signal to generate a voltage signal, wherein the input signal is generated in response to an ultrasonic wave reflecting off an item-to-be-imaged and propagating via a piezoelectric layer; a noise reduction circuit configured to pass the voltage signal from an output of the amplifier to a node, while reducing a propagation of noise from the output of the amplifier to the node; and a circuit configured to generate a DC pixel voltage based on the reduced-noise voltage signal.

10 Claims, 7 Drawing Sheets

(56) References Cited

OTHER PUBLICATIONS

Chen K., et al., "Ultrasonic Imaging Transceiver Design for CMUT: A Three-Level 30-Vpp Pulse-Shaping Pulser With Improved Efficiency and a Noise-Optimized Receiver", IEEE Solid-State Circuits Society, IEEE Service Center, Piscataway, NJ, USA, Nov. 1, 2013 (Nov. 1, 2013 ), XP011531079, vol. 48, No. 11, pp. 2734-2745, ISSN: 0018-9200, DOI: 10.11 09/JSSC.2013.2274895 [retrieved on Oct. 21, 2013].
International Search Report and Written Opinion—PCT/US2016/044011—ISA/EPO—dated Nov. 28, 2016.

* cited by examiner

PIXEL RECEIVER WITH LOW FREQUENCY NOISE REDUCTION FOR ULTRASONIC IMAGING APPARATUS

BACKGROUND

Field

Aspects of the present disclosure relate generally to ultrasonic imaging apparatuses, and more particularly, to a pixel receiver with low frequency noise reduction for use in an ultrasonic imaging apparatus.

Background

An ultrasonic imaging apparatus may be used for obtaining electronic or digital images of certain items, such as fingerprints. An ultrasonic imaging apparatus typically comprises an ultrasonic wave transmitter including a transmitting piezoelectric layer (e.g., such as a polyvinylidene fluoride (PVDF) layer), a receiving piezoelectric layer (e.g., a PVDF layer), and a pixel receiver comprising a two-dimensional array of pixel sensors. Generally, the ultrasonic wave transmitter is situated below the pixel receiver, and the pixel receiver is situated below the receiving piezoelectric layer. The item-to-be-imaged, such as a user's fingerprint, is positioned above the receiving piezoelectric layer.

In operation, the transmitting piezoelectric layer of the ultrasonic wave transmitter is excited to generate an ultrasonic wave (e.g., a 10 MHz ultrasonic wave) upwards through the pixel receiver and the receiving piezoelectric layer until the wave encounters the item-to-be-imaged, such as a user's fingerprint. The ultrasonic wave reflects off the fingerprint and propagates downward towards the pixel receiver. The receiving piezoelectric layer converts the reflected wave into voltages at respective inputs of the pixel sensors of the pixel receiver. The voltages generated at the inputs of the pixel sensors are a function of whether the corresponding wave encountered a valley or ridge of the user's fingerprint.

The pixel sensors process the respective high frequency voltages to generate DC output pixel voltages. An analog-to-digital converter is provided to digitize the DC output pixel voltages. The digitized signals may then be processed by an image processor to perform various operations, such as fingerprint recognition, fingerprint database storage, and others.

In the past, the pixel receiver has been implemented using thin-film transistor (TFT) technology. However, circuits implemented using TFT technology generally have less voltage conversion efficiency and more noise than circuits implemented using other technology, such as complementary metal oxide semiconductor (CMOS) technology.

SUMMARY

The following presents a simplified summary of one or more embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later.

An aspect of the disclosure relates to an apparatus for generating a DC pixel voltage. The apparatus comprises an amplifier configured to amplify an input signal to generate a voltage signal, wherein the input signal is generated in response to an ultrasonic wave reflecting off an item-to-be-imaged and propagating via a piezoelectric layer; a noise reduction circuit configured to pass the voltage signal from an output of the amplifier to a node, while reducing a propagation of noise from the output of the amplifier to the node; and a circuit configured to generate the DC pixel voltage based on the reduced-noise voltage signal.

Another aspect of the disclosure relates to a method of generating a PC pixel voltage. The method comprises amplifying an input signal to generate a voltage signal, wherein the input signal is generated in response to an ultrasonic wave reflecting off an item-to-be-imaged and propagating via a piezoelectric layer; reducing noise from the voltage signal; and generating the DC pixel voltage based on the reduced-noise voltage signal.

Another aspect of the disclosure relates to an apparatus for generating a DC pixel voltage. The apparatus comprises means for amplifying an input signal to generate a voltage signal, wherein the input signal is generated in response to an ultrasonic wave reflecting off an item-to-be-imaged and propagating via a piezoelectric layer; means for reducing noise from the voltage signal; and means for generating the DC pixel voltage based on the reduced-noise voltage signal.

To the accomplishment of the foregoing and related ends, the one or more embodiments comprise the features hereinafter fully described and particularly pointed out in the claims. The following description and the annexed drawings set forth in detail certain illustrative aspects of the one or more embodiments. These aspects are indicative, however, of but a few of the various ways in which the principles of various embodiments may be employed and the description embodiments are intended to include all such aspects and their equivalents.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details. In some instances, well-known structures and components are shown in block diagram form in order to avoid obscuring such concepts.

Figure 1:
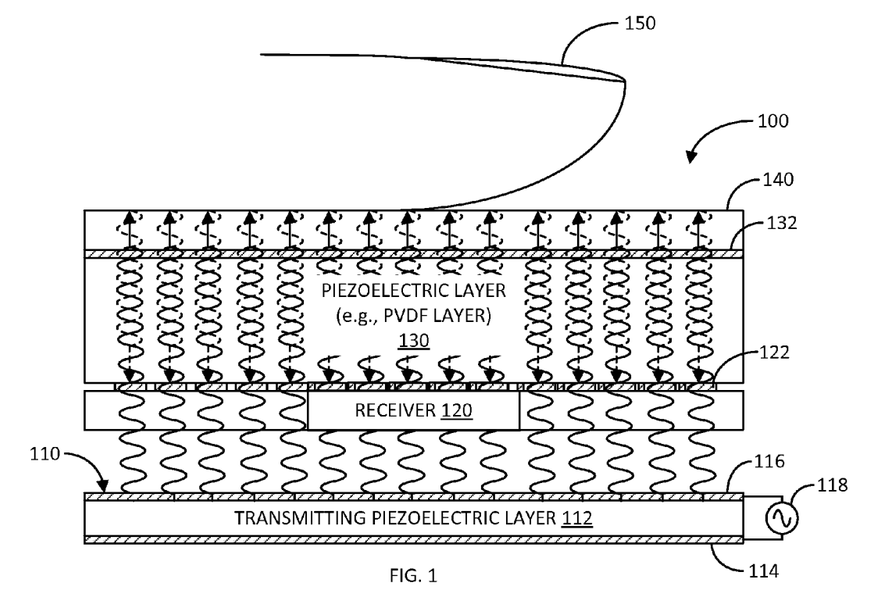
FIG. 1 illustrates a side cross-sectional view of an exemplary ultrasonic imaging apparatus in accordance with an aspect of the disclosure.

FIG. 1 illustrates a side cross-sectional view of an exemplary ultrasonic imaging apparatus 100 in accordance with an aspect of the disclosure. The ultrasonic imaging apparatus 100 comprises an ultrasonic wave transmitter 110 configured to generate an ultrasonic wave (e.g., a 10 MHz ultrasonic wave). The ultrasonic transmitter 110 is configured to generate the ultrasonic wave so that it propagates upwards through various layers, as discussed further herein.

More specifically, the ultrasonic wave transmitter 110 may comprise a transmitting piezoelectric layer 112, a pair of electrodes 114 and 116 coupled to the transmitting piezoelectric layer 112, and an excitation source 118. The piezoelectric layer 112 may comprise a polyvinylidene fluoride (PVDF) layer or other type of piezoelectric layer. The excitation source 118 is configured to generate an excitation voltage for the transmitting piezoelectric layer 112 such that layer emits an ultrasonic wave at a desired frequency (e.g., 10 MHz).

The ultrasonic imaging apparatus 100 further comprises a pixel receiver 120 positioned above the ultrasonic wave transmitter 110. A spacer (not shown), such as a glass spacer, may be sandwiched between the ultrasonic wave transmitter 110 and pixel receiver 120. As discussed further herein, the pixel receiver 120 comprises a two-dimensional array of pixel sensors configured to receive and process respective voltages associated with the item-to-be-imaged, such as a user's fingerprint. The pixel receiver 120 comprises a plurality of input metallization pads 122 arranged in a two-dimensional array for receiving input pixel voltages associated with the item-to-be-imaged.

The ultrasonic imaging apparatus 100 further comprises a receiving piezoelectric layer 130 disposed on and/or positioned above the pixel receiver 120. The receiving piezoelectric layer 130 converts the ultrasonic wave reflected off of the item-to-be-imaged (e.g., user's fingerprint) into input pixel voltages for the pixel sensors of the pixel receiver 120. Similarly, the receiving piezoelectric layer 130 may comprise a polyvinylidene fluoride (PVDF) layer or other type of piezoelectric layer. An electrode 132 (e.g., metallization layer) may be provided on top of the receiving piezoelectric layer 130 for receiving a potential (e.g., ground or other) for different operations.

The ultrasonic imaging apparatus 100 further comprises a platen 140 disposed over the electrode 132. The platen 140 serves as a protective coating for the components of the ultrasonic imaging apparatus 100 underlying the platen. Additionally, the platen 140 serves to provide a surface upon which the item-to-be-imaged, such as a user's finger 150, may be placed, as illustrated in FIG. 1.

In operation, the ultrasonic wave transmitter 110 is operated to generate a burst of ultrasonic wave (e.g., a 10 MHz ultrasonic wave) propagating upwards towards the user's finger 150 by way of the pixel receiver 120, receiving piezoelectric layer 130, and platen 140. The incident ultrasonic wave upon the user's finger 150 produces a reflected ultrasonic wave, which propagates downward through the receiving piezoelectric layer 130. The piezoelectric layer 130 converts the reflected wave into voltages at the respective inputs 122 of the pixel sensors of the receiver 120. The amplitude of each of the voltages depends on whether the corresponding reflected ultrasonic wave portion encountered a ridge or a valley of the fingerprint. The pixel sensors process the input pixel voltages to generate corresponding direct current (DC) pixel voltages for further digitizing and processing in accordance with the desired imaging application.

Figure 2:
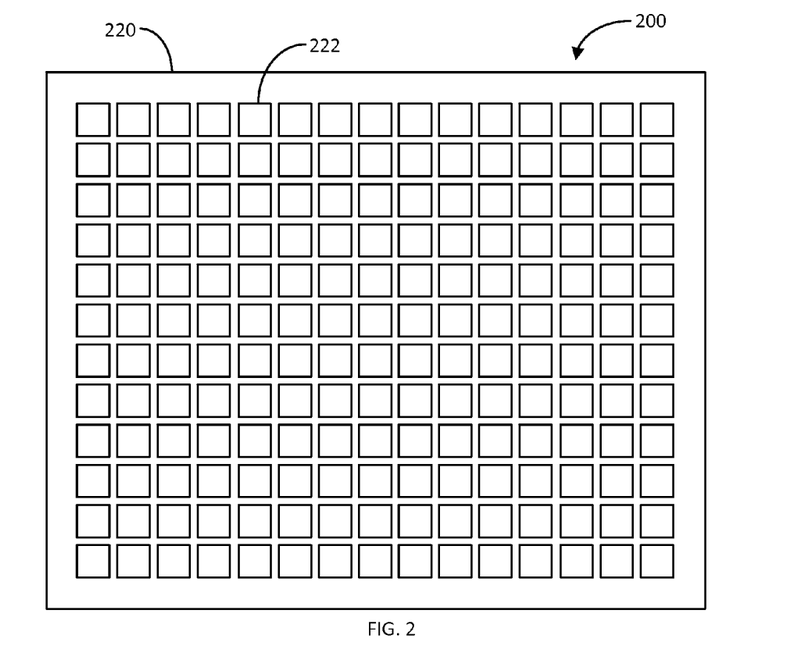
FIG. 2 illustrates a top view of an exemplary CMOS receiver for an ultrasonic imaging apparatus in accordance with another aspect of the disclosure.

FIG. 2 illustrates a top view of an exemplary CMOS receiver 200 for an ultrasonic imaging apparatus in accordance with another aspect of the disclosure. The CMOS receiver 200 may be an exemplary detailed implementation of the pixel receiver 120 of ultrasonic imaging apparatus 100 previously discussed.

The CMOS receiver 200 comprises a CMOS integrated circuit (IC) 220 including an array of pixel sensors. A top portion of the CMOS IC 220 includes a plurality of input metallization pads 222 arranged in a two-dimensional array. Although not shown in FIG. 2, the CMOS receiver 200 may include a dielectric passivation layer disposed over the array of input metallization pads 222. The receiving piezoelectric layer 130 may be attached to the top surface of the CMOS IC 220 using, for example, an adhesive material. The metallization pads 222 serve as the respective inputs to the pixel sensors of the CMOS receiver 200, where input pixel voltages related to the corresponding reflected ultrasonic wave are developed.

Figure 3:
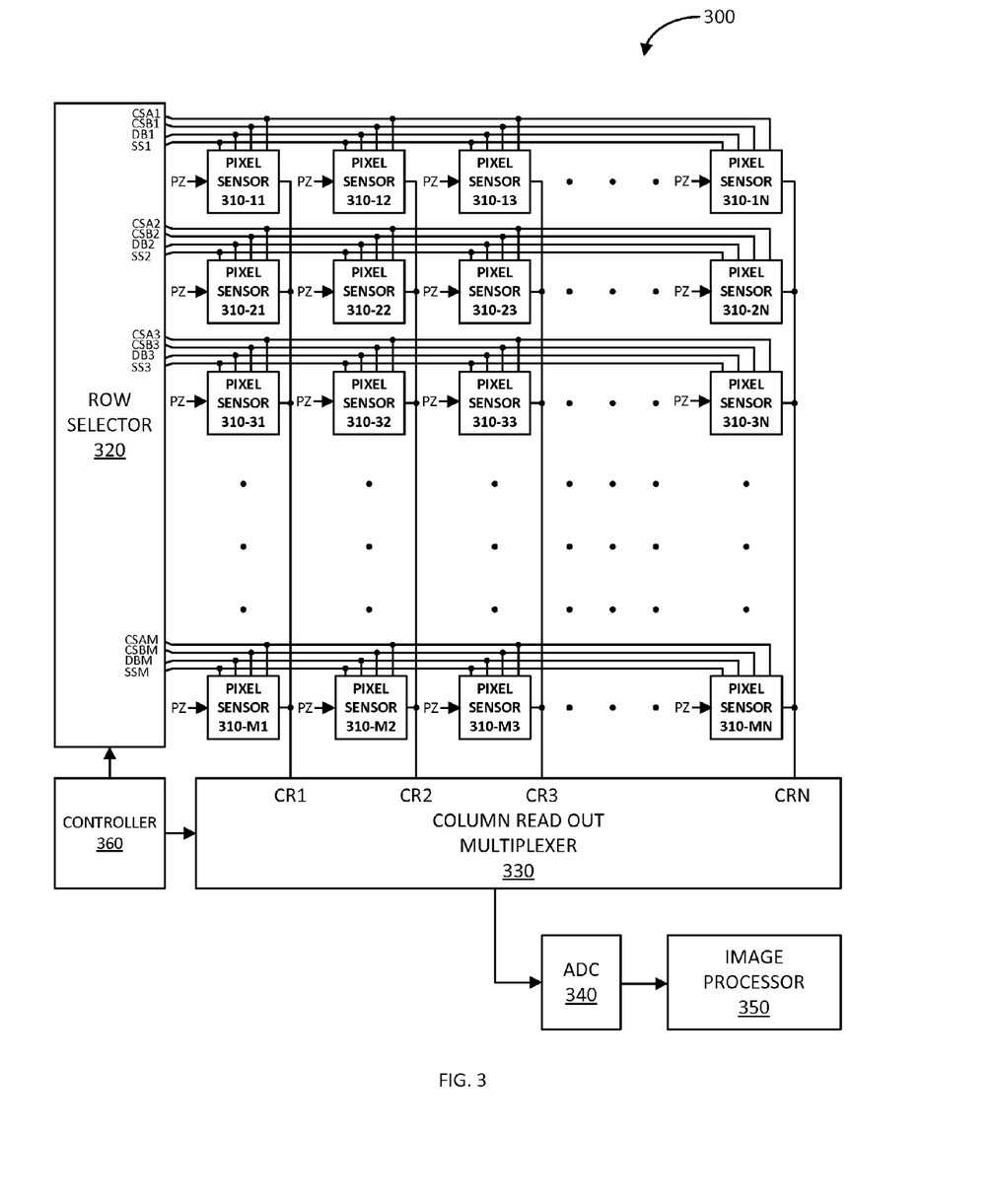
FIG. 3 illustrates a schematic diagram of an exemplary CMOS receiver for an ultrasonic imaging apparatus in accordance with another aspect of the disclosure.

FIG. 3 illustrates a schematic diagram of an exemplary CMOS receiver 300 for an ultrasonic imaging apparatus in accordance with another aspect of the disclosure. The CMOS receiver 300 may be an exemplary detailed implementation of either or both the receiver 120 and the CMOS receiver 200, previously discussed.

In particular, the CMOS receiver 300 comprises a two-dimensional array of pixel sensors 310-11 to 310-MN. In this example, the size of the pixel sensor array is M×N. That is, the pixel sensor array has M rows of pixel sensors and N columns of pixel sensors. Pixel sensors 310-11 to 310-1N are in the first row of the array; pixel sensors 310-21 to 310-2N are in the second row of the array; pixel sensors 310-31 to 310-3N are in the third row of the array; and pixel sensors 310-M1 to 310-MN are in the Mth row of the array. Similarly, pixel sensors 310-11 to 310-M1 are in the first column of the array; pixel sensors 310-12 to 310-M2 are in the second column of the array; pixel sensors 310-13 to 310-M3 are in the third column of the array; and pixel sensors 310-1N to 310-MN are in the Nth column of the array. As shown, all the of pixel sensors 310-11 to 310-MN are coupled to piezoelectric (PZ) layer for receiving respective input pixel voltages therefrom.

The CMOS receiver 300 further comprises a row selector 320, a column read out multiplexer 330, an analog-to-digital converter (ADC) 340, an image processor 350, and a controller 360. The row selector 320, under the control of the controller 360, activates a row of pixel sensors for the purposes of generating corresponding output DC pixel voltages. In this regard, the row selector 320 generates four signals CSA1/CSB1/DB1/SS1 to CSAM/CSBM/DBM/SSM for the rows 310-11/310-1N to 310-M1/310-MN, respectively.

As discussed in more detail herein, the CSA1 to CSAM signals clear feedback capacitors of charge of corresponding pixel sensors. The CSB1 to CSBM signals set common mode voltages for amplified voltage signals generated by corresponding pixel sensors. The DB1 to DBM signals are used to enable peak detectors for generating DC pixel voltages related to the peak of the amplified voltage signals of the corresponding pixel sensors. The SS1 to SSM signals causes the DC pixel voltages generated by the corresponding pixel sensors to be applied to corresponding column read out lines CR1 to CRN.

Under the control of the controller 360, the column read out multiplexer 330 reads out the output DC pixel voltages from the pixel sensors of the activated row. The multiplexer 330 may output the DC pixel voltages in a serial manner to the ADC 340. It shall be understood that the multiplexer 330 may be configured to output at least a portion of the DC pixel voltages in parallel to a plurality of ADCs, respectively. The ADC 340 digitizes the DC pixel voltages and provides them to the image processor 350. The image processor 350 may perform any number of operations based on the received digitized pixel voltages. For example, the image processor 350 may perform fingerprint recognition based on a previously-stored authenticated fingerprint image.

Figure 4A:
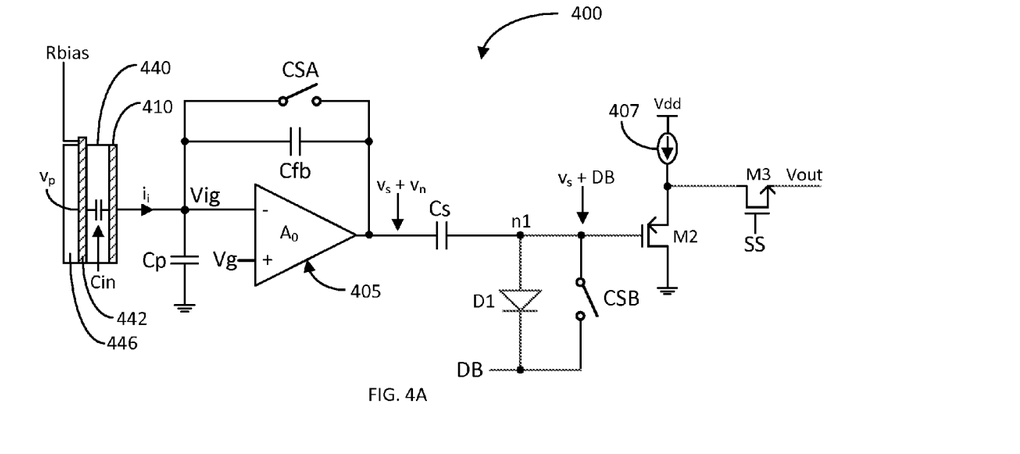
FIG. 4A illustrates a schematic diagram of an exemplary pixel sensor for an ultrasonic imaging apparatus in accordance with another aspect of the disclosure.

FIG. 4A illustrates a schematic diagram of an exemplary pixel sensor 400 for an ultrasonic imaging apparatus in accordance with another aspect of the disclosure. The pixel sensor 400 may be an exemplary detailed implementation of any of the pixel sensors 310-11 to 310-MN previously discussed. As illustrated, the pixel sensor 400 comprises an input metallization pad 410 coupled to a receiving piezoelectric layer 440. As previously discussed, an electrode 442 is disposed over the receiving piezoelectric layer 440, and a platen 446 is disposed over the electrode 442. An item-to-be-image, such as a fingerprint, may be placed over the platen 442. The electrode 442 may be configured to receive an Rbias voltage, which could be at ground potential or other potential.

The pixel sensor 400 comprises a transimpedance amplifier (TIA) 405 including a positive input, a negative input, and an output. The TIA 405 further comprises a feedback capacitor Cfb coupled between the output and the negative input. The positive input of the TIA 405 is configured to receive a reference DC voltage Vg. The negative input of the TIA 405 is coupled to the input metallization pad of the pixel sensor 400. As the pixel sensor 400 may be implemented using a complementary metal oxide semiconductor (CMOS) technology, the TIA 405 may be implemented with a field effect transistor (FET) formed over a grounded substrate. As such, a parasitic capacitance Cp may exist between the input metallization layer 410 and the grounded substrate.

In such configuration, the TIA 405 is configured to amplify an input current signal $i_i$ based on a voltage $v_p$ generated by the piezoelectric layer 440 in response to an ultrasonic wave burst reflecting off an item-to-be-imaged disposed over the platen 446. Assuming the TIA 405 has a very high open-loop gain $A_0$ (e.g., a cascode configuration), the voltage Vig at the negative input may be substantially the same as the reference DC voltage Vg at the positive input of the TIA. As such, the TIA 405 is configured to amplify the input voltage, $v_p$ with a closed-loop gain $A_{cl}$ that may be given substantially by the following relationship:

$$A_{cl} = \frac{Cin}{Cfb}$$

where Cfb is the capacitance of the feedback capacitor Cfb, and Cin is the sense capacitance of the piezoelectric layer 440.

Additionally, the pixel sensor 400 comprises a controllable switch CSA coupled between the output and negative input of the TIA 405. The controllable switch CSA is configured to be controlled by a corresponding one of the control signals CSA1 to CSAM generated by the row selector 320, as previously discussed. The corresponding control signal closes and opens the switch CSA at particular times to clear the feedback capacitor Cfb of any charge that may be remaining from a previous operation cycle. The TIA 405 is configured to generate a voltage signal $v_s$ that may be given substantially by the following relationship:

$$v_s = v_p * A_{cl} = v_p * \frac{Cin}{Cfb} = \frac{i_i}{Cfb}$$

It should be noted that because the TIA 405 is configured to amplify the input current signal $i_i$, the voltage signal $v_s$ generated by the TIA 405 is substantially independent of the parasitic capacitance Cp. Or, said differently, the sensitivity of the pixel sensor 400 is substantially less dependent on the parasitic capacitance Cp.

Additionally, to further minimize the effects of parasitic capacitance Cp on the sensitivity of the pixel sensor 400, the TIA 405 may be implemented using one or more small devices or FETs. However, small devices generate more low frequency noise. Accordingly, the pixel sensor 400 further comprises circuitry to perform first order noise shaping or reduction of the voltage signal $v_s$ generated by the TIA 405. In this regard, the pixel sensor 400 further comprises a capacitor Cs, a diode D1, and a controllable switch CSB. The capacitor Cs is coupled between the output of the TIA 405 and an intermediate node n1. The diode D1 includes an anode coupled to the intermediate node n1 and a cathode coupled to a source of a diode bias (DB) voltage (e.g., the row selector 320, which generates a corresponding one of the signals DB1 to DBM). The controllable switch CSB is coupled between the intermediate node n1 and the DB voltage source. The controllable switch CSB is configured to be controlled by a corresponding one of the control signals CSB1 to CSBM generated by the row selector 320, as previously discussed.

The pixel sensor 400 further comprises an output circuit including p-channel MOSFET ("PMOS") M2, current source 407, and n-channel MOSFET ("NMOS") M3. The PMOS M2 is configured as a source-follower amplifier (e.g., having approximately a unity gain) including a source coupled to a drain of NMOS M3, a gate coupled to the intermediate node n1, and a drain coupled to ground. The current source 407 is coupled between a voltage rail Vdd and the source of PMOS M2. The NMOS M3, in turn, includes a gate configured to receive signal SS and a source coupled to the corresponding column read out line. The signal SS may be a corresponding one of the signals SS1 to SSM generated by the row selector 320. The output DC pixel voltage Vout is produced at the source of NMOS M3.

Figure 4B:
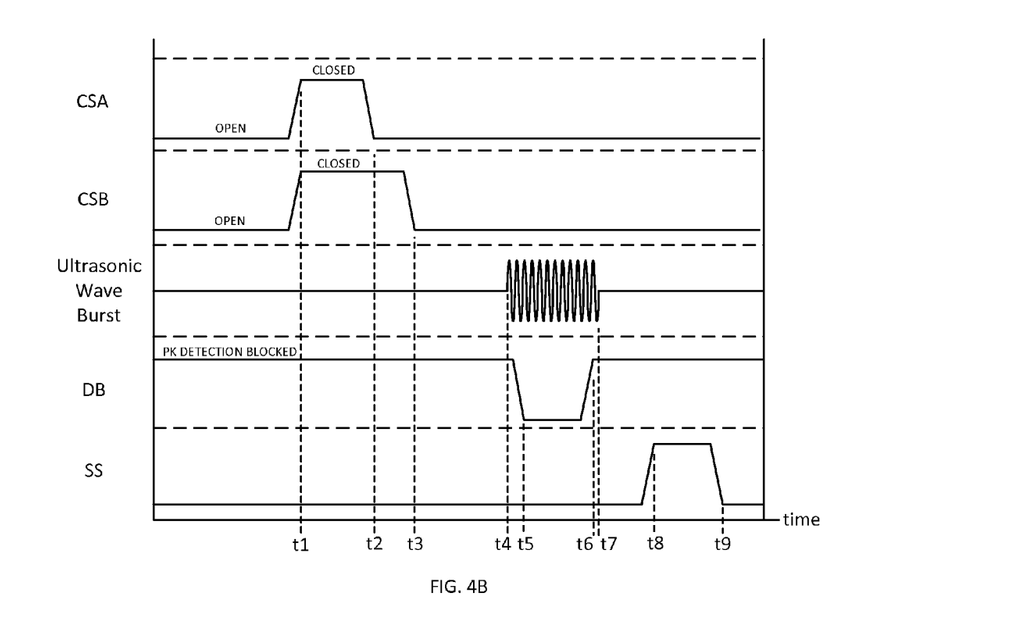
FIG. 4B illustrates a timing diagram associated with an exemplary operation of the pixel sensor of FIGS. 4A, 5, and 6 in accordance with another aspect of the disclosure.

FIG. 4B illustrates a timing diagram associated with an exemplary operation of the pixel sensor 400 in accordance with another aspect of the disclosure. The horizontal or x-axis of the timing diagram represents time, the vertical axis represents the states or amplitudes of the CSA, CSB, ultrasonic wave burst, DB, and SS.

According to the timing diagram, at time t1, the CSA and CSB are brought to asserted states to close switches CSA and CSB. The closing of switch CSA clears any charge that may be present on the feedback capacitor Cfb from, for example, a previous operation cycle of the pixel sensor 400. The closing of switch CSB is configured to apply the DB voltage to the intermediate node n1 to set a common mode voltage for the subsequent voltage signal generated at the intermediate node n1. After a defined time interval sufficient to clear the charge from feedback capacitor Cfb, at time t2, the switch CSA is opened. When the switch CSA is opened, switch and low frequency noise $v_n$ is produced at the output of the TIA 405. The capacitor Cs prevents the noise $v_n$ from ending up at the intermediate node n1 because of its high pass frequency characteristic, and the intermediate node n1 is connected to the DB voltage. This is part of the first order noise shaping or reduction that occurs at the output of the TIA 405. After a defined time interval to effectuate the first order noise shaping, at time t3, the switch CSB is opened.

At time t4, the ultrasonic transmitter is enabled to generate an ultrasonic wave burst through the receiving piezoelectric layer 440, electrode 442, and platen 446. As previously discussed, the ultrasonic wave burst reflects off a user's finger and back into the piezoelectric layer 440 to produce an input voltage signal $v_p$ (e.g., 10 MHz input voltage signal). The amplitude of the input voltage signal is a function of whether the corresponding reflected ultrasonic wave encountered a ridge or valley of the user's fingerprint, i.e., a function of the item-to-be-imaged.

In response to the input pixel voltage $v_p$, an input current signal $i_i$ is generated, which is amplified by the TIA 405 to generate an amplified voltage signal $v_s$. Accordingly, the amplitude of the voltage signal $v_s$ is based on the reflected ultrasonic wave, which, in turn, is based on the item-to-be-imaged (e.g., a user's fingerprint). As the voltage signal $v_s$ alternates with substantially the same frequency as the ultrasonic wave (e.g., 10 MHz), the capacitor Cs allows the voltage signal $v_s$ to pass to the intermediate node n1, while maintaining at least a portion of the low frequency noise $v_n$ at the output of the TIA 405. Again, this is part of the first order noise shaping or reduction that occurs at the output of the TIA 405.

At time t5, the DB voltage is lowered (asserted state) to enable the peak detection of the voltage signal $v_s$ performed by the diode D1. As the peaks of the voltage signal $v_s$ forward bias the diode D1, current is generated through the diode D1 to charge a parasitic capacitor across the diode. Thus, a DC pixel voltage at the intermediate node n1 is developed based on one or more peaks of the voltage signal $v_s$. Thus, as discussed, since the voltage signal $v_s$ is based on the item-to-be-imaged, the DC pixel voltage is also based on the item-to-be imaged. After a sufficient time interval to develop the DC pixel voltage, at time t6, the DB voltage is brought up to its original level (de-asserted state), and at time t7, the ultrasonic wave transmitter is disabled to cease generating the ultrasonic wave burst.

After the DC pixel voltage has been developed at the intermediate node n1, at time t8, the SS is brought up to an asserted state in order to turn on NMOS M3, and produce an output DC pixel voltage Vout at the corresponding column read out line by way of the source-follower PMOS M2. After a sufficient time interval for the column read out multiplexer 330 to read out the output DC pixel voltage Vout, the SS is brought down to its de-asserted state to complete the operation cycle of the pixel sensor 400.

Figure 5:
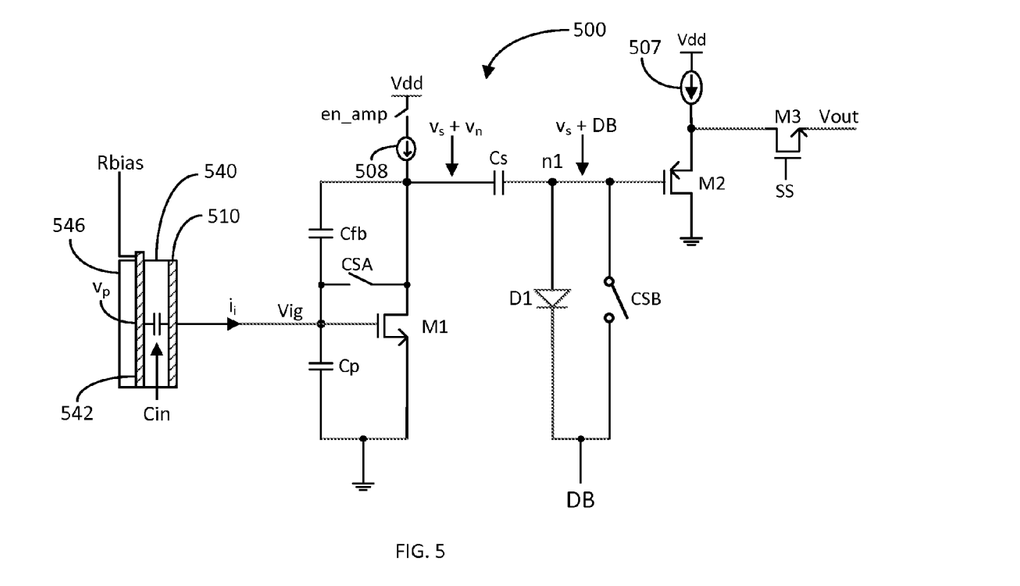
FIG. 5 illustrates a schematic diagram of another exemplary pixel sensor for an ultrasonic imaging apparatus in accordance with another aspect of the disclosure.

FIG. 5 illustrates a schematic diagram of another exemplary pixel sensor 500 for an ultrasonic imaging apparatus in accordance with another aspect of the disclosure. The pixel sensor may be an exemplary more detail implementation of the pixel sensor 400. Similar elements in pixel sensor 500 include the same identifiers, and the same reference numbers except with the most significant digit being a "5" instead of a "4".

In summary, the pixel sensor 500 comprises a transimpedance amplifier (TIA) to amplify an input current signal $i_i$ (based on a voltage $v_p$ generated by a piezoelectric layer 540 in response to an ultrasonic wave reflecting off an item-to-be-imaged) to generate an amplified voltage signal $v_s$; a first order noise shaping or reduction circuit to reduce low frequency noise from the voltage signal $v_s$; a peak detector to generate a DC pixel voltage based on one or more peaks of the reduced-noise voltage signal $v_s$; and an output circuit to selectively provide an output DC pixel voltage Vout to a column read out line.

In particular, the pixel sensor 500 comprises an input metallization pad 510 coupled to a receiving piezoelectric layer 540. Similar to pixel sensor 400, an electrode 542 is disposed over the receiving piezoelectric layer 540, and a platen 546 is disposed over the electrode 542. An item-to-be-image, such as a fingerprint, may be placed over the platen 542. The electrode 542 may be configured to receive an Rbias voltage, which could be at ground potential or other potential.

The pixel sensor 500 comprises an NMOS M1 configured to perform transimpedance amplification of an input current signal $i_i$ to generate a voltage signal $v_s$. The input current signal $i_i$ is generated in response to an ultrasonic wave reflecting off an item-to-be-imaged and propagating via the piezoelectric layer 540. The NMOS M1 includes a gate coupled to the input metallization pad 510, a source coupled to ground, and a drain to serve as an output for generating the voltage signal $v_s$. As the NMOS M1 may be implemented on a CMOS IC substrate, a parasitic capacitance Cp may exist between the input metallization layer 510 and the grounded substrate.

The pixel sensor 500 further comprises a feedback capacitor Cfb coupled between the drain and gate of the NMOS M1. Additionally, a controllable switch CSA is also coupled between the drain and gate of the NMOS M1. A switch en_amp and a current source 508 are coupled in series with the NMOS M1 between a voltage rail Vdd and ground. The switch en_amp is closed to enable transimpedance amplification of the input current signal $i_i$ implemented by the NMOS M1, and opened to disable the transimpedance amplification. A bias voltage Vig is developed at the gate of NMOS M1 while the controllable switch CSA is closed. In such configuration, the NMOS M1 provides a closed-loop gain $A_{cl}$ that may be given substantially by the following relationship:

$$A_{cl} = \frac{Cin}{Cfb}$$

where Cfb is the capacitance of the feedback capacitor Cfb, and Cin is the sense capacitance of the piezoelectric layer 540.

The controllable switch CSA is configured to be controlled by a corresponding one of the control signals CSA1 to CSAM generated by the row selector 320, as previously discussed. The corresponding control signal closes and opens the switch CSA at particular times to clear the feedback capacitor Cfb of any charge that may be remaining from a previous operation cycle, and to develop the bias voltage Vig at the gate of NMOS M1. The NMOS M1 is configured to generate the voltage signal $v_s$ that may be given substantially by the following relationship:

$$v_s = v_p * A_{cl} = v_p * \frac{Cin}{Cfb} = \frac{i_i}{Cfb}$$

It should be noted that if an open-loop gain $A_0$ provided by the NMOS M1 is high (which could be made high with one or more additional devices for cascode operation), the voltage signal $v_s$ may be substantially independent of the parasitic capacitance Cp. Or, said differently, the sensitivity of the pixel sensor 500 may not be significantly affected by the parasitic capacitance Cp.

Additionally, to further minimize the effects of the parasitic capacitance Cp on the sensitivity of the pixel sensor 500, the NMOS M1 (and accompanying one or more cascode devices) may be made relatively small. However, as previously discussed, small devices generate more low frequency noise. Accordingly, the pixel sensor 500 further comprises circuitry to perform first order noise shaping or reduction of the voltage signal $v_s$ generated at the drain of the NMOS M1. In this regard, the pixel sensor 500 further includes a capacitor Cs, a diode D1, and a controllable switch CSB.

The capacitor Cs is coupled between the drain of NMOS M1 and an intermediate node n1. The diode D1 includes an anode coupled to the intermediate node n1 and a cathode coupled to a source of a diode bias (DB) voltage (e.g., the row selector 320, which generates a corresponding one of the signals DB1 to DBM). The controllable switch CSB is coupled between the intermediate node n1 and the DB voltage source. The controllable switch CSB is configured to be controlled by a corresponding one of the control signals CSB1 to CSBM generated by the row selector 320, as previously discussed.

The pixel sensor 500 further comprises an output circuit including p-channel MOSFET ("PMOS") M2, current source 507, and n-channel MOSFET ("NMOS") M3. The PMOS M2 is configured as a source-follower amplifier (e.g., having approximately unity gain) including a source coupled to a drain of NMOS M3, a gate coupled to the intermediate node n1, and a drain coupled to ground. The current source 507 is coupled between a voltage rail Vdd and the source of PMOS M2. The NMOS M3, in turn, includes a gate configured to receive signal SS and a source coupled to the corresponding column read out line. The signal SS may be a corresponding one of the signals SS1 to SSM generated by the row selector 320. The output DC pixel voltage generated by the pixel sensor 500 is produced at the source of NMOS M3.

The timing diagram of FIG. 4A is applicable to the operation of the pixel sensor 500. Although not reflected by the timing diagram, the en_amp switch is closed and opened at the beginning and end of the operations cycle so as to enable the transimpedance amplification implemented by the NMOS M1.

In particular, at time t1, the switches CSA and CSB are closed. The switch CSA is closed to clear the feedback capacitor Cfb of any charge that may be present from, for example, a previous operation cycle of the pixel sensor 500. The closing of the switch CSA also produces a gate bias voltage Vig for the NMOS M1. The switch CSB is closed to develop a common mode voltage DB at the intermediate node n1. At times t2, the switch CSA is opened, which causes switch and low frequency noise $v_n$ to be generated at the drain of the NMOS M1. However, the noise $v_n$ does not propagate to the intermediate node n1 due to the first order noise shaping or reduction performed by the capacitor Cs tied to the DB voltage via the closed CSB switch. At time t3, the switch CSB is opened.

At time t4, the ultrasonic wave transmitter is enabled to generate an ultrasonic wave bursts. As previously discussed, the ultrasonic wave burst produces an input current signal $i_i$. The NMOS M1 applies a transimpedance amplification to the input current signal $i_i$ to generate a voltage signal $v_s$ at the drain of NMOS N1. Since the voltage signal $v_s$ cycles with substantially the same frequency as the ultrasonic wave (e.g., 10 MHz), the high pass filter characteristic of the capacitor Cs allows the voltage signal $v_s$ to pass to the intermediate node n1, while maintaining at least a portion of the noise $v_n$ from propagating to the intermediate node n1. At time t5, the DB voltage is lowered to enable the peak detection of the voltage signal $v_s$ performed by the diode D1. The peak detection produces a DC pixel voltage at the intermediate node n1.

After a sufficient time interval for developing the DC pixel voltage at the intermediate node n1, at time t6, the DB voltage is brought up to its original voltage level to disable the peak detection performed by the diode D1. Then, at time t8, the SS signal is brought up to an asserted state to turn on NMOS M3 to apply the output DC pixel voltage Vout to the corresponding column read out line by way of the source-follower PMOS M2. After a sufficient time interval for the column read out multiplexer 330 to read out the output DC pixel voltage Vout, the SS signal is brought down to its de-asserted state to turn off NMOS M3, and complete the operation cycle of the pixel sensor 500.

Figure 6:
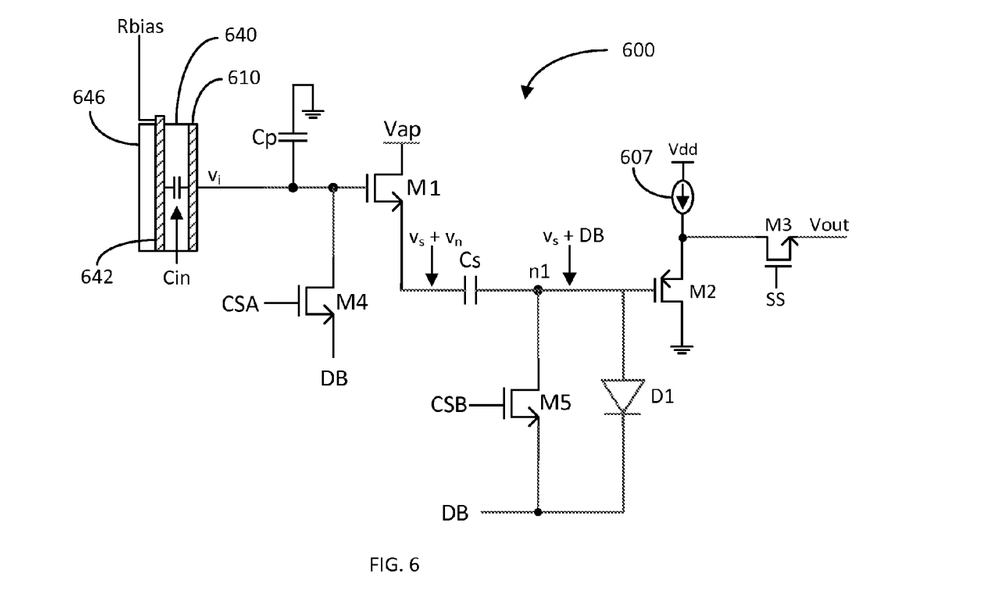
FIG. 6 illustrates a schematic diagram of another exemplary pixel sensor for an ultrasonic imaging apparatus in accordance with another aspect of the disclosure.

FIG. 6 illustrates a schematic diagram of another exemplary pixel sensor 600 for an ultrasonic imaging apparatus in accordance with another aspect of the disclosure. The pixel sensor 600 includes similar elements as pixel sensor 500, which may be identified by the same component identifiers, and the same reference numbers except with the most significant digit being a "6" instead of a "5".

In summary, the pixel sensor 600 comprises a source-follower amplifier configured to amplify an input voltage signal $v_i$ (generated in response to an ultrasonic wave reflecting off an item-to-be-imaged and propagating via a piezoelectric layer) to generate an amplified voltage signal $v_s$; a first order noise shaping or reduction to low frequency noise from the voltage signal $v_s$; a peak detector for generating a DC pixel voltage based on one or more peaks of the amplified voltage signal $v_s$; and an output circuit to selectively output the DC pixel voltage to a column read out line.

In particular, the pixel sensor 600 comprises an input metallization pad 610 coupled to a receiving piezoelectric layer 640. As in the previous embodiments, an electrode 642 is disposed over the receiving piezoelectric layer 640, and a platen 646 is disposed over the electrode 642. An item-to-be-image, such as a fingerprint, may be placed over the platen 642. The electrode 642 may be configured to receive an Rbias voltage, which could be at ground potential or other potential.

The pixel sensor 600 comprises an NMOS M1 configured as a source-follower amplifier to amplify an input voltage signal vi developed at the input metallization pad 610 with substantially a unity voltage gain. The input voltage signal $v_i$ is generated in response to an ultrasonic wave reflecting off an item-to-be-imaged and propagating via the piezoelectric layer 640. The NMOS M1 includes a gate coupled to the input metallization pad 610, a drain coupled to a bias voltage rail Vap, and a source to generate an output voltage signal $v_s$. As the NMOS M1 may be implemented on a CMOS IC substrate, a parasitic capacitance Cp may exist between the input metallization layer 610 and the grounded substrate.

The pixel sensor 600 further comprises another NMOS M4 coupled between the gate of the NMOS M1 and a source of the DB voltage (e.g., the row selector 320). The NMOS M4 includes a gate configured to receive a control signal CSA, which could be a corresponding one of the control signals CSA1 to CSAM generated by the row selector 320. The control signal CSA turns on and off the NMOS M4 at particular times to clear the gate of NMOS M1 of any charge remaining from, for example, a previous operation cycle of the pixel sensor 600. Additionally, the turning on of NMOS M4 is also done to develop the bias voltage for the gate of NMOS M1.

To reduce the effects of the parasitic capacitance Cp on the sensitivity of the pixel sensor 600, the NMOS M1 may be made relatively small. However, as previously discussed, small devices generate more low frequency noise. Accordingly, the pixel sensor 600 further comprises circuitry to perform first order noise shaping or reduction at the output of the source-follower amplifier (NMOS M1). In this regard, the pixel sensor 600 further includes a capacitor Cs, a diode D1, and a NMOS M5. The capacitor Cs is coupled between the source of NMOS M1 and an intermediate node n1. The diode D1 includes an anode coupled to the intermediate node n1 and a cathode coupled to the source of the DB voltage (e.g., the row selector 320). The NMOS M5 is coupled between the intermediate node n1 and the DB voltage source. The NMOS M5 includes a gate configured to receive a control signal CSB, which may be a corresponding one of the control signals CSB1 to CSBM generated by the row selector 320, as previously discussed.

The pixel sensor 600 further comprises an output circuit including p-channel MOSFET ("PMOS") M2, current source 607, and n-channel MOSFET ("NMOS") M3. The PMOS M2 is configured as a source-follower amplifier (e.g., having approximately unity gain) including a source coupled to a drain of NMOS M3, a gate coupled to the intermediate node n1, and a drain coupled to ground. The NMOS M3, in turn, includes a gate configured to receive signal SS and a source coupled to the corresponding column read out line. The signal SS may be a corresponding one of the signals SS1 to SSM generated by the row selector 320. The output DC pixel voltage generated by the pixel sensor 600 is produced at the source of NMOS M3.

The timing diagram of FIG. 4A is applicable to the operation of the pixel sensor 600. For example, at time t1, NMOS M4 and M5 are turned on. NMOS M4 is closed to clear the gate of any charge that may be present on the gate of NMOS M1 from, for example, a previous operation cycle of the pixel sensor 600. The turning on of NMOS M4 also produces a gate bias voltage for the NMOS M1. The NMOS M5 is turned on to develop a common mode voltage DB at the intermediate node n1. At times t2, the NMOS M4 is turned off, which causes switch and low frequency noise $v_n$ to be generated at the output (source) of the source-follower amplifier (NMOS M1). However, the noise $v_n$ does not propagate to the intermediate node n1 due to the first order noise shaping or high pass filtering performed by the capacitor Cs tied to the DB voltage via NMOS M5. At time t3, the NMOS M5 is turned off.

At time t4, the ultrasonic wave transmitter is enabled to generate an ultrasonic wave bursts. As previously discussed, the ultrasonic wave burst produces an input voltage signal $v_i$. The NMOS M1, which is configured as a source-follower, amplifies the input voltage signal $v_i$ with substantially unity gain to generate an amplified voltage signal $v_s$ at the source of NMOS N1. Since the voltage signal $v_s$ cycles with substantially the same frequency as the ultrasonic wave (e.g., 10 MHz), the high pass filter characteristic of the capacitor Cs allows the voltage signal $v_s$ to pass to the intermediate node n1, while substantially preventing the noise $v_n$ to pass to the intermediate node n1. At time t5, the DB voltage is lowered to enable the peak detection of the voltage signal $v_s$ performed by the diode D1. The peak detection produces a DC pixel voltage.

After a sufficient time interval for developing the DC pixel voltage, at time t6, the DB voltage is brought up to its original voltage level to disable the peak detection performed by the diode D1. Then, at time t8, the SS signal is brought up to an asserted state to turn on NMOS M3 to apply the output DC pixel voltage Vout to the corresponding column read out line. After a sufficient time interval for the column read out multiplexer 330 to read out the output DC pixel voltage Vout, the SS signal is brought down to its de-asserted state to turn off NMOS M3, and complete the operation cycle of the pixel sensor 600.

Figure 7:
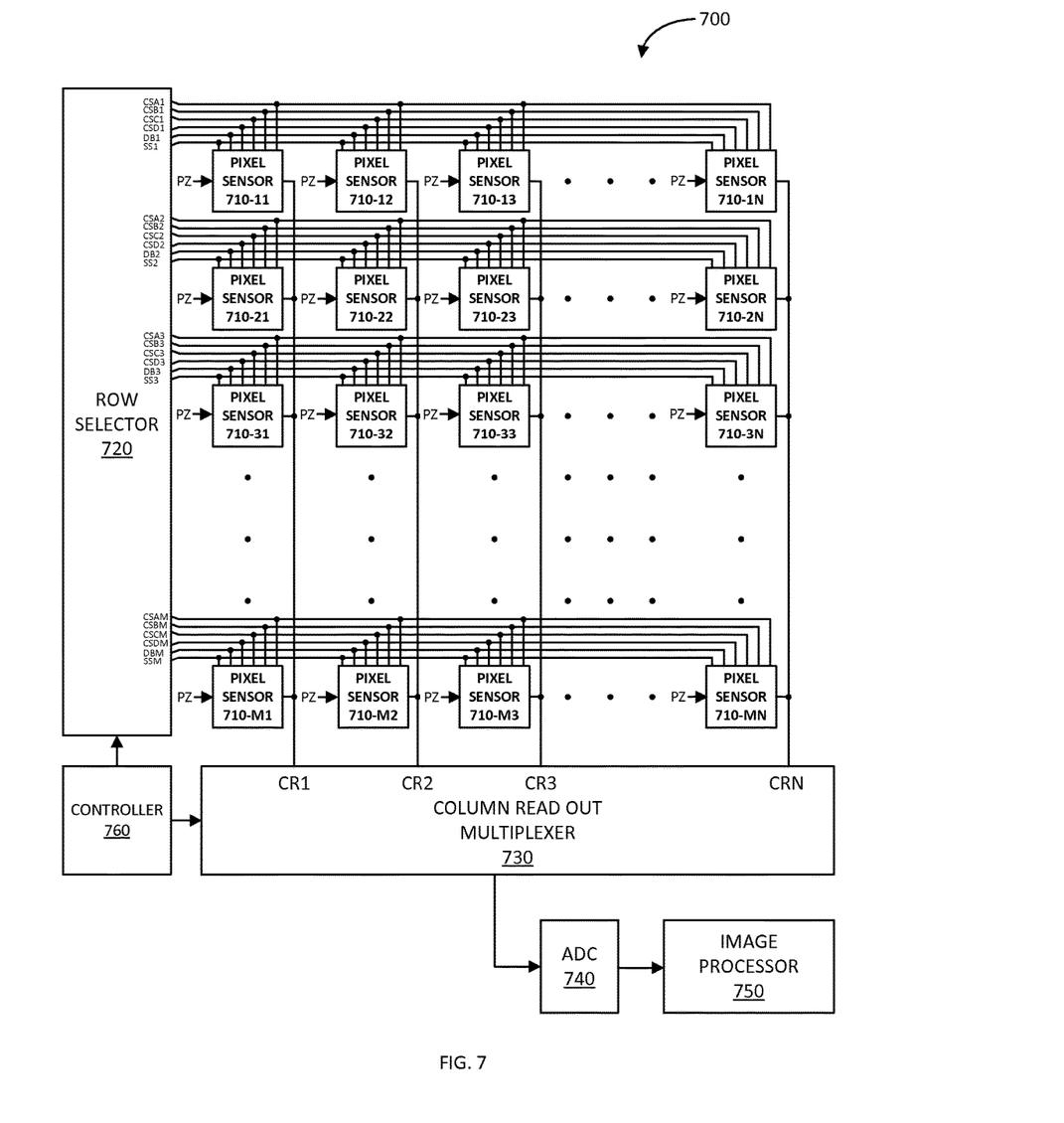
FIG. 7 illustrates a schematic diagram of another exemplary CMOS receiver for an exemplary ultrasonic imaging apparatus in accordance with another aspect of the disclosure.

FIG. 7 illustrates a schematic diagram of an exemplary CMOS receiver 700 for an ultrasonic imaging apparatus in accordance with another aspect of the disclosure. The CMOS receiver 700 is similar to that of CMOS receiver 300 previously discussed, and includes many similar elements as indicated by the same reference numbers with the most significant digit being a "7" instead of a "3". The CMOS receiver 700 differs from CMOS 300 in that the row selector 720 generates additional signals to operate pixel sensors.

More specifically, the CMOS receiver 700 comprises pixel sensors 710-11 to 710-MN, arranged in a two-dimensional array of M rows and N columns, wherein the pixel sensors are coupled to a receiving piezoelectric layer (PZ). The CMOS receiver 700 further comprises a row selector 720 configured to generate control signals CSA1/CSB1/CSC1/CSD1/DB1/SS1 to CSAM/CSBM/CSCM/CSDM/DBM/SSM for pixel sensors 710-11/710-1N to 710-M1/710-MN, respectively. Additionally, the CMOS receiver 700 includes a column read out multiplexer 730 configured to read out output DC pixel voltages generated by the pixel sensors via column read out lines CR1 to CRN.

The CMOS 700 further comprises a controller 760 for controlling the operations of the row selector 720 and the column read out multiplexer 730. Further, the CMOS receiver 700 comprises an analog-to-digital converter (ADC) 740 for converting the read out DC pixel voltages into digital pixel signals, and an image processor 750 to process the digital pixel signals based on one or more defined applications.

The signals CSA1/CSB1/DB1/SS1 to CSAM/CSBM/DBM/SSM generated by the row selector 720 have been discussed with reference to row selector 320 of CMOS receiver 300. In addition to these signals, the row selector 720 generates control signals CSC1/CSD1 to CSCM/CSDM. As discussed in more detail further herein, the CSC1 to CSCM signals are for setting a common mode voltage at an output of a transimpedance (TIA) amplifier of the corresponding pixel sensor. The CSD1 to CSDM are for decoupling the output of the TIA amplifier from an intermediate node n1 during a peak of a voltage signal $v_s$ for peak detection of the signal, as discussed in more detail further herein.

Figure 8A:
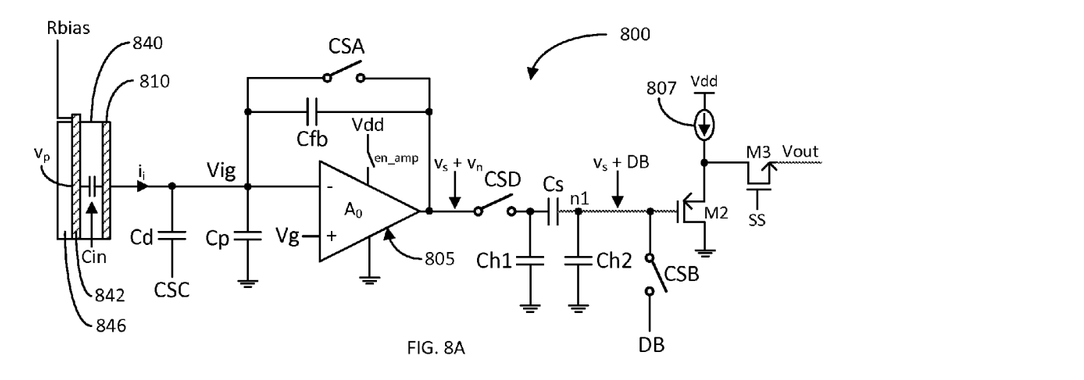
FIG. 8A illustrates a schematic diagram of another exemplary pixel sensor for an ultrasonic imaging apparatus in accordance with another aspect of the disclosure.

FIG. 8A illustrates a schematic diagram of another exemplary pixel sensor 800 for an ultrasonic imaging apparatus in accordance with another aspect of the disclosure. The pixel sensor 800 may be an exemplary detailed implementation of any of the pixel sensors 710-11 to 710-MN previously discussed. As illustrated, the pixel sensor 800 comprises an input metallization pad 810 coupled to a receiving piezoelectric layer 840. As previously discussed, an electrode 842 is disposed over the receiving piezoelectric layer 840, and a platen 846 is disposed over the electrode 842. An item-to-be-image, such as a fingerprint, may be placed over the platen 842. The electrode 842 may be configured to receive an Rbias voltage, which could be at ground potential or other potential.

The pixel sensor 800 comprises a transimpedance amplifier (TIA) 805 including a positive input, a negative input, and an output. The TIA 805 further comprises a feedback capacitor Cfb coupled between the output and the negative input. The positive input of the TIA 805 is configured to receive a reference DC voltage Vg. The negative input of the TIA 805 is coupled to the input metallization pad 810. As the pixel sensor 800 may be implemented using CMOS technology, the TIA 805 may be implemented with one or more FETs formed over a grounded substrate. As such, a parasitic capacitance Cp may exist between the input metallization layer 810 and the grounded substrate.

In such configuration, the TIA 805 is configured to amplify an input current signal $i_i$ based on a voltage $v_p$ generated by the piezoelectric layer 840 in response to an ultrasonic wave burst reflecting off an item-to-be-imaged disposed over the platen 846. Assuming the TIA 805 has a very high open-loop gain $A_0$ (e.g., a cascode configuration), the voltage Vig at the negative input may be substantially the same as the reference DC voltage Vg at the positive input of the TIA. As such, the TIA 805 is configured to amplifying the input voltage signal $v_p$ with a closed-loop gain $A_{cl}$ that may be given substantially by the following relationship:

$$A_{cl} = \frac{Cin}{Cfb}$$

where Cfb is the capacitance of the feedback capacitor Cfb, and Cin is the sense capacitance of the piezoelectric layer 840.

Additionally, the pixel sensor 800 comprises a controllable switch CSA coupled between the output and negative input of the TIA 805. The controllable switch CSA is configured to be controlled by a corresponding one of the control signals CSA1 to CSAM generated by the row selector 720, as previously discussed. The corresponding control signal closes and opens the switch CSA at particular times to clear the feedback capacitance Cfb of any charge that may be remaining from a previous operation cycle. The TIA 805 is configured to generate an amplified voltage signal $v_s$ that may be given substantially by the following relationship:

$$v_s = v_i * A_{cl} = v_i * \frac{Cin}{Cfb} = \frac{i_i}{Cfb}$$

It should be noted that because the TIA 805 is configured to amplify the input current signal $i_i$, the voltage signal $v_s$ generated by the TIA 805 may be substantially independent of the parasitic capacitance Cp. Or, said differently, the sensitivity of the pixel sensor 800 is not significantly affected by the parasitic capacitance Cp.

The pixel sensor 800 further comprises a capacitor Cd coupled between the negative input of the TIA 805 and a source of control signal CSC (e.g., the row selector 720). The control signal CSC may be a corresponding one of the control signals CSC1 to CSCM generated by the row selector 720. The signal CSC is configured to set a common mode voltage at the output of the TIA 805 (e.g., VDD/2). Additionally, the TIA 805 may be enabled and disabled via an en_amp signal, as discussed further herein.

To further minimize the effects of the parasitic capacitance Cp on the sensitivity of the pixel sensor 800, the TIA 805 may be implemented using one or more small devices or FETs. However, as previously discussed, small devices generate more low frequency noise. Accordingly, the pixel sensor 800 further comprises circuitry to perform first order noise shaping or reduction at the output of the TIA 805. In this regard, the pixel sensor 800 further comprises a controllable switch CSD, a capacitor Cs, sample and hold capacitors Ch1 and Ch2, and a controllable switch CSB.

The controllable switch CSD is coupled between the output of the TIA 805 and a first end of the capacitor Cs. The capacitor Cs includes a second end coupled to an intermediate node n1. The capacitor Ch1 is coupled between the first end of the capacitor Cs and ground. The capacitor Ch2 is coupled between the intermediate node n1 and ground. The controllable switch CSB is coupled between the intermediate node n1 and a source of a DB voltage (e.g., row selector 720). The controllable switch CSB is configured to be controlled by a corresponding one of the control signals DB1 to DBM generated by the row selector 720, as previously discussed.

The pixel sensor 800 further comprises an output circuit including p-channel MOSFET ("PMOS") M2, current source 807, and n-channel MOSFET ("NMOS") M3. The PMOS M2 is configured as a source-follower amplifier (e.g., having approximately a unity gain) including a source coupled to a drain of NMOS M3, a gate coupled to the intermediate node n1, and a drain coupled to ground. The current source 807 is coupled between a voltage rail Vdd and the source of PMOS M2. The NMOS M3, in turn, includes a gate configured to receive signal SS and a source coupled to the corresponding column read out line. The signal SS may be a corresponding one of the signals SS1 to SSM generated by the row selector 720. The output DC pixel voltage Vout is produced at the source of NMOS M3.

Figure 8B:
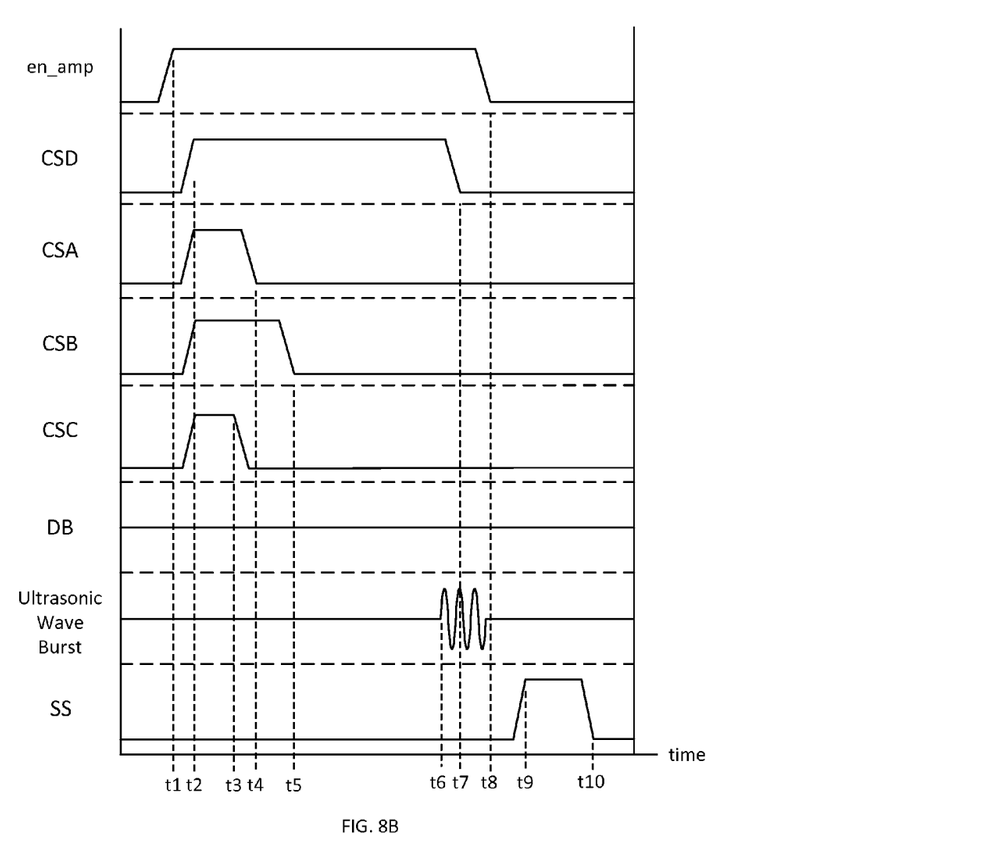
FIG. 8B illustrates a timing diagram associated with an exemplary operation of the pixel sensor of FIG. 8A in accordance with another aspect of the disclosure.

FIG. 8B illustrates a timing diagram associated with an exemplary operation of the pixel sensor 800 in accordance with another aspect of the disclosure. The horizontal or x-axis of the timing diagram represents time, the vertical axis represents the states or amplitudes of the CSD, CSA, CSB, CSC, DB, ultrasonic wave burst, and SS.

According to the timing diagram, at time t1, the en_amp signal is brought up to an asserted state to enable the TIA 805. At time t2, the CSD, CSA, CSB, and CSC are brought to asserted states to close switches CSD, CSA, and CSB, and set CSC to a defined voltage level. The closing of switch CSD couples the output of the TIA 805 to the capacitor Cs. The closing of switch CSA clears the feedback capacitor Cfb of any charge that may be present from, for example, a previous operation cycle of the pixel sensor 800. The closing of switch CSB is configured to apply the DB voltage to the intermediate node n1 to set a common mode voltage for the subsequent signal generated at the intermediate node n1. And, the setting of CSC to the defined voltage level is for setting a common mode voltage at the output of the TIA 805 (e.g., Vdd/2). At time t3, the CSC voltage is lowered to its original level.

At time t4, the switch CSA is opened. When the switch CSA is opened, switch and low frequency noise $v_n$ may be produced at the output of the TIA 805. The capacitor Cs prevents the noise $v_n$ from ending up at the intermediate node n1 because of the high pass filter characteristic of the capacitor Cs. This is part of the first order noise shaping or reduction that occurs at the output of the TIA 805. After a defined time interval to effectuate the first order noise shaping, at time t4, the switch CSB is opened.

At time t6, the ultrasonic transmitter is enabled to generate an ultrasonic wave burst through the receiving piezoelectric layer 840, electrode 842, and platen 846. As previously discussed, the ultrasonic wave bursts reflects off a user's finger and back into the piezoelectric layer 840. In response to the reflected ultrasonic wave bursts, the input current signal $i_i$ is generated. The input current signal $i_i$ cycles at substantially the same frequency as the ultrasonic wave (e.g., 10 MHz), and has an amplitude as a function of whether the corresponding reflected ultrasonic wave encountered a ridge or valley of the user's fingerprint, i.e., as a function of the item-to-be-imaged.

The TIA 805 amplifies the input voltage signal $v_p$ with the closed-loop gain $A_{cl}$ to generate an amplified voltage signal $v_s$. Accordingly, the amplitude of the voltage signal $v_s$ is also based on the reflected ultrasonic wave, which, in turn, is based on the item-to-be-imaged (e.g., a user's fingerprint). As the voltage signal $v_s$ also alternates with substantially the same frequency as the ultrasonic wave (e.g., 10 MHz), the capacitor Cs allows the voltage signal $v_s$ to pass to the intermediate node n1, while maintaining the low frequency noise $v_n$ at the output of the TIA 805. Again, this is part of the first order noise shaping or reduction that occurs at the output of the TIA 805.

At time t7, the switch CSD is opened at a time that substantially coincides with a peak (or other portion) of the amplified voltage signal $v_s$. The capacitor Ch2 sample and holds the peak value of the voltage signal $v_s$ at the intermediate node n1. Accordingly, the DC pixel voltage is developed at the intermediate node n1, which is based substantially on the peak of the voltage signal $v_s$. Thus, as discussed, since the amplitude or peak of the voltage signal $v_s$ is based on the item-to-be-imaged, the DC pixel voltage is also based on the item-to-be imaged. At time t8, the ultrasonic wave transmitter is disabled to cease the generation of the ultrasonic wave bursts, and the en_amp signal is brought to the de-asserted state to disable the TIA 805.

At time t9, the SS is brought up to an asserted level in order to turn on NMOS M3, and output DC pixel voltage Vout at the corresponding column read out line by way of the source-follower PMOS M2. After a sufficient time interval for the column read out multiplexer 730 to read out the output DC pixel voltage Vout, at time t10, the SS is brought down to its de-asserted state to complete the operation cycle of the pixel sensor 800.

Figure 9:
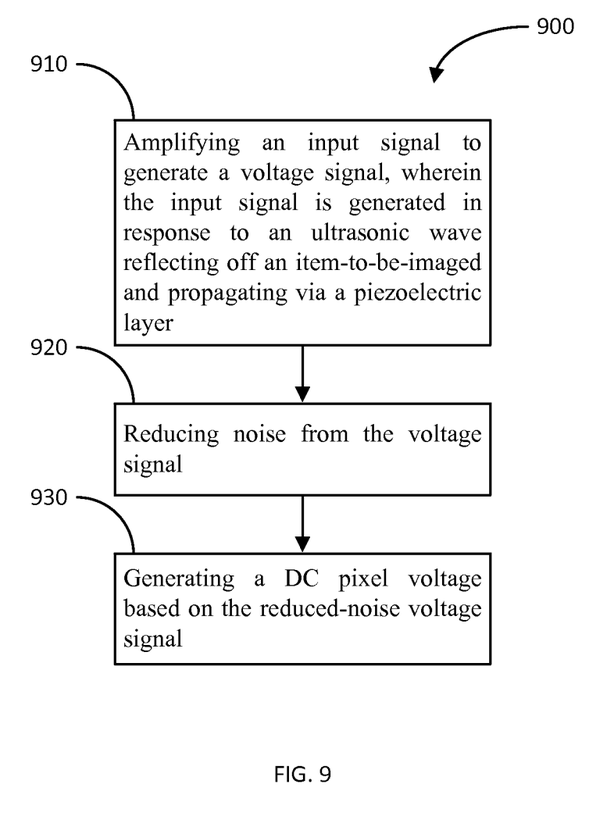
FIG. 9 illustrates a flow diagram of an exemplary method of generating a DC pixel voltage by a pixel sensor in accordance with another aspect of the disclosure.

FIG. 9 illustrates a flow diagram of an exemplary method 900 of generating a DC pixel voltage in accordance with another aspect of the disclosure. The method 900 comprises amplifying an input signal to generate a voltage signal, wherein the input signal is generated in response to an ultrasonic wave reflecting off an item-to-be-imaged and propagating via a piezoelectric layer (block 910). The method 900 further comprises reducing noise from the voltage signal (block 920). And, the method 900 comprises generating a DC pixel voltage based on the reduced-noise voltage signal (block 930).

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples described herein but is to be accorded the widest scope consistent with the principles and novel features disclosed herein.

What is claimed is:

1. An apparatus, comprising:
   an amplifier configured to amplify an input signal to generate a voltage signal, wherein the input signal is generated in response to an ultrasonic wave reflecting off an item-to-be-imaged and propagating via a piezoelectric layer;
   a noise reduction circuit configured to pass the voltage signal from an output of the amplifier to a node, while reducing a propagation of noise from the output of the amplifier to the node; and
   a circuit configured to generate a DC pixel voltage based on the voltage signal at the node.

2. The apparatus of claim 1, wherein the noise reduction circuit comprises a capacitor coupled between the amplifier and the node.

3. The apparatus of claim 1, wherein the noise comprises low frequency noise generated by the amplifier.

4. The apparatus of claim 1, wherein the input signal comprises an input current signal, and the amplifier comprises a transimpedance amplifier configured to perform transimpedance amplification of the input current signal to generate the voltage signal.

5. The apparatus of claim 4, wherein a gain associated with the transimpedance amplification is based on a sense capacitance of the piezoelectric layer.

6. The apparatus of claim 4, wherein a gain associated with the transimpedance amplification is based on a ratio of a capacitance of a feedback capacitor coupled between the output and an input of the amplifier over a sense capacitance of the piezoelectric layer.

7. The apparatus of claim 1, wherein the amplifier comprises a source-follower amplifier.

8. The apparatus of claim 1, wherein the circuit comprises a peak detector configured to generate the DC pixel voltage based substantially on one or more peaks of the voltage signal.

9. The apparatus of claim 1, wherein the circuit comprises a sample and hold circuit configured to generate the DC pixel voltage based substantially on a sampled portion of the voltage signal.

10. The apparatus of claim 1, further comprising an output circuit configured to selectively output the DC pixel voltage.

* * * * *